(12) United States Patent
Kinomoto

(10) Patent No.: US 12,138,120 B2
(45) Date of Patent: Nov. 12, 2024

(54) ULTRASONIC ENDOSCOPE

(71) Applicant: FUJIFILM Corporation, Tokyo (JP)

(72) Inventor: Noboru Kinomoto, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 135 days.

(21) Appl. No.: 17/900,877

(22) Filed: Sep. 1, 2022

(65) Prior Publication Data

US 2022/0409175 A1 Dec. 29, 2022

Related U.S. Application Data

(63) Continuation of application No. PCT/JP2021/011306, filed on Mar. 19, 2021.

(30) Foreign Application Priority Data

Mar. 26, 2020 (JP) ................................. 2020-055657

(51) Int. Cl.
*A61B 8/00* (2006.01)
*A61B 1/00* (2006.01)
(Continued)

(52) U.S. Cl.
CPC .......... *A61B 8/445* (2013.01); *A61B 1/00082* (2013.01); *A61B 1/015* (2013.01);
(Continued)

(58) Field of Classification Search
CPC ........... A61B 1/06; A61B 8/445; A61B 1/015; A61B 1/0082; A61B 8/4494; A61B 8/12
See application file for complete search history.

(56) References Cited

U.S. PATENT DOCUMENTS

2019/0125305 A1 5/2019 Tsuruta
2019/0209124 A1* 7/2019 Taniguchi ............ A61B 8/4461

FOREIGN PATENT DOCUMENTS

JP H08280686 10/1996
JP 2009207758 9/2009
(Continued)

OTHER PUBLICATIONS

"Office Action of Japan Counterpart Application", issued on Sep. 20, 2023, with English translation thereof, p. 1-p. 4.
(Continued)

*Primary Examiner* — Joel F Brutus
(74) *Attorney, Agent, or Firm* — JCIPRNET

(57) ABSTRACT

Provided is an ultrasonic endoscope with which it is possible to improve a brush cleanability of a communication path. A distal end portion (44) of an ultrasonic endoscope (10) includes: a balloon attachment portion (152) for attachably and detachably attaching a balloon (60) to the distal end portion (44), the balloon attachment portion (152) including a first balloon groove (154) that is provided over an outer periphery of the distal end portion at least on a proximal end side of an ultrasound oscillator (92); and a communication path (90) for supply or suction of a fluid with respect to an inner space of the balloon (60). An entrance and exit way (91) of the communication path (90) is formed to be diagonally inclined with respect to a longitudinal axis of an insertion portion (12). The first balloon groove (154) includes a shallow groove portion (158) that is formed to have a groove depth smaller than other portions in a circumferential direction of the distal end portion (44), and the entrance and exit way (91) of the communication path (90) is provided in an internal region of the distal end portion (44) where the shallow groove portion (158) is formed.

5 Claims, 6 Drawing Sheets

(51) Int. Cl.
*A61B 1/015* (2006.01)
*A61B 1/06* (2006.01)
*A61B 8/12* (2006.01)
*A61B 90/70* (2016.01)

(52) U.S. Cl.
CPC ............... *A61B 1/06* (2013.01); *A61B 8/12* (2013.01); *A61B 8/4494* (2013.01); *A61B 2090/701* (2016.02)

(56) References Cited

FOREIGN PATENT DOCUMENTS

| JP | 2011083410 | 4/2011 |
| WO | 2015156903 | 10/2015 |
| WO | 2017149815 | 9/2017 |

OTHER PUBLICATIONS

"International Search Report (Form PCT/ISA/210) of PCT/JP2021/011306," mailed on May 18, 2021, with English translation thereof, pp. 1-5.
"Written Opinion of the International Searching Authority (Form PCT/ISA/237) of PCT/JP2021/011306," mailed on May 18, 2021,, with English translation thereof, pp. 1-6.

* cited by examiner

ULTRASONIC ENDOSCOPE

CROSS-REFERENCE TO RELATED APPLICATIONS

The present application is a Continuation of PCT International Application No. PCT/JP2021/0011306 filed on Mar. 19, 2021 claiming priority under 35 U.S.C § 119(a) to Japanese Patent Application No. 2020-055657 filed on Mar. 26, 2020. Each of the above applications is hereby expressly incorporated by reference, in its entirety, into the present application.

BACKGROUND OF THE INVENTION

1. Field of the Invention

The present invention relates to an ultrasonic endoscope, and particularly to an ultrasonic endoscope in which a balloon can be mounted on a distal end portion of an insertion portion to be inserted into a body cavity.

2. Description of the Related Art

An ultrasonic endoscope is used in the medical field. Regarding the ultrasonic endoscope, an imaging element and an ultrasonic transducer are integrally disposed at a distal end portion of an insertion portion which is to be inserted into a body cavity of a subject. The ultrasonic transducer generates an ultrasonic wave toward an observation target site in the body cavity and receives an echo signal reflected from the observation target site, and an electric signal corresponding to the received echo signal is output to an ultrasonic observation device. Then, after various types of signal processing are performed in the ultrasonic observation device, the result thereof is displayed on a monitor or the like in the form of an ultrasonic tomographic image.

Since ultrasonic waves and echo signals are significantly attenuated in air, it is necessary to interpose an ultrasonic wave transmitting medium such as water or oil between the ultrasonic transducer and the observation target site. Therefore, an elastic balloon is mounted on a distal end portion of the ultrasonic endoscope, and the ultrasonic wave transmitting medium is injected into the balloon so that the balloon is inflated and is brought into contact with the observation target site. Accordingly, air is removed from between the ultrasonic transducer and the observation target site, and thus attenuation of ultrasonic waves and of echo signals is prevented.

For supply of the ultrasonic wave transmitting medium into the balloon and discharge of the ultrasonic wave transmitting medium or for supply of air for inflating the balloon or discharge of the air, a communication path is inserted into the insertion portion of the ultrasonic endoscope. The communication path includes a distal end opening that is open at the distal end portion of the insertion portion, and the ultrasonic wave transmitting medium or air is supplied into the balloon or is discharged via the distal end opening.

The ultrasonic endoscope needs to be cleaned and disinfected after an examination, and the communication path needs to be brushed. Described in JP2015-156903A below is an ultrasonic endoscope in which an entrance and exit way of a balloon adsorption pipe line and/or a balloon water injection pipe line (corresponding to "communication path") is inclined with respect to an axis of an insertion portion so that cleaning a communication path with a cleaning brush is facilitated, for example.

SUMMARY OF THE INVENTION

However, in the case of a configuration in which an entrance and exit way of a communication path is diagonally inclined with respect to the axis of an insertion portion, there are the following problems. That is, in a case where the entrance and exit way is inclined without changing a position of the distal end opening of the communication path, the entrance and exit way is disposed close to an outer side in comparison with a case where the entrance and exit way of the communication path is formed to be perpendicular to a longitudinal axis of the distal end portion, and thus a balloon groove to which a proximal end side end portion of a balloon is attached and the entrance and exit way interfere with each other. Therefore, it is necessary to move the balloon groove to the proximal end side. In a case where the balloon groove is disposed on the proximal end side, the total length of the distal end portion becomes large, and the radius of a distal end portion trajectory becomes large in a case where a bendable portion is bent, which requires a larger space.

The present invention has been made in consideration of such circumstances, and an object thereof is to provide an ultrasonic endoscope with which it is possible to prevent the length of a distal end portion from becoming large and to improve a brush cleanability.

An ultrasonic endoscope according to an aspect of the present invention is a radial type ultrasonic endoscope in which an ultrasound oscillator is provided at a distal end portion of an insertion portion and in which an observation system and an illumination system are disposed closer to a distal end side than the ultrasound oscillator. The distal end portion includes: a balloon attachment portion for attachably and detachably attaching a balloon to the distal end portion, the balloon attachment portion including a first balloon groove that is provided over an outer periphery of the distal end portion at least on a proximal end side of the ultrasound oscillator; and a communication path for supply or suction of a fluid with respect to an inner space of the balloon attached to the distal end portion, the communication path including an entrance and exit way that is open into the inner space of the balloon. The entrance and exit way of the communication path is formed to be diagonally inclined with respect to a longitudinal axis of the insertion portion, the first balloon groove includes a shallow groove portion that is formed to have a groove depth smaller than other portions in a circumferential direction of the distal end portion, and the entrance and exit way of the communication path is provided in an internal region of the distal end portion where the shallow groove portion is formed.

In an aspect of the present invention, the balloon attachment portion preferably includes a second balloon groove that is provided over the outer periphery of the distal end portion on a distal end side of the ultrasound oscillator, and a depth of the second balloon groove is preferably uniform in the circumferential direction of the distal end portion.

In an aspect of the present invention, in a cross section orthogonal to the longitudinal axis of the insertion portion, a shape of a bottom surface of the first balloon groove is preferably a shape obtained by swelling a circle toward a position where the entrance and exit way is provided.

In an aspect of the present invention, a central axis of the ultrasound oscillator and a central axis of the distal end portion preferably coincide with each other.

In an aspect of the present invention, a portion of the communication path that is closer to the proximal end side than the entrance and exit way is preferably formed to be parallel with the longitudinal axis of the insertion portion.

According to the aspects of the present invention, it is possible to prevent the length of a distal end portion from becoming large and to improve a brush cleanability of a communication path.

DESCRIPTION OF THE PREFERRED EMBODIMENTS

Hereinafter, preferred embodiments of an ultrasonic endoscope according to an embodiment of the present invention will be described with reference to the accompanying drawings.

Figure 1:
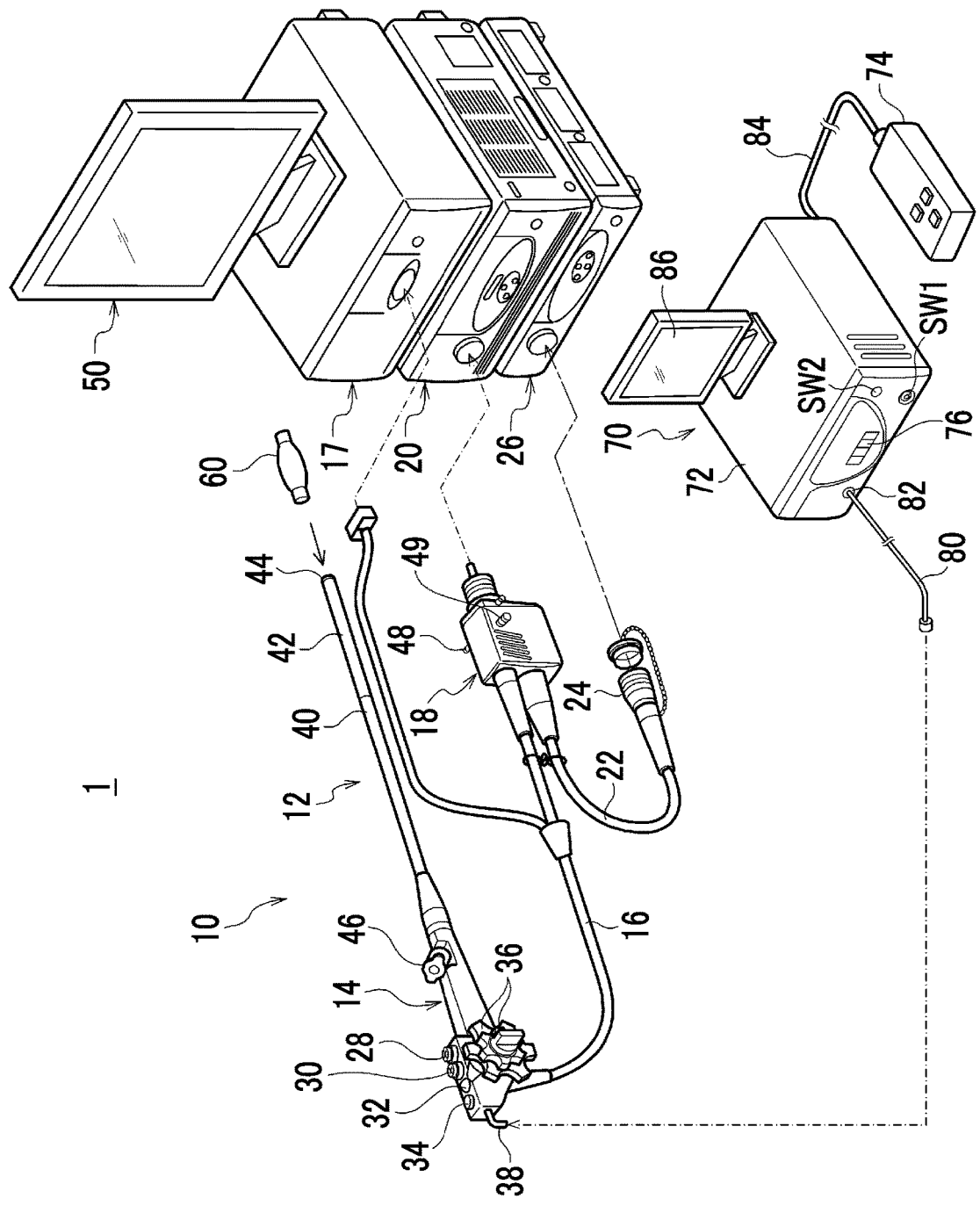
FIG. 1 is a system configuration view of an endoscope apparatus including an ultrasonic endoscope.
Figure 2:
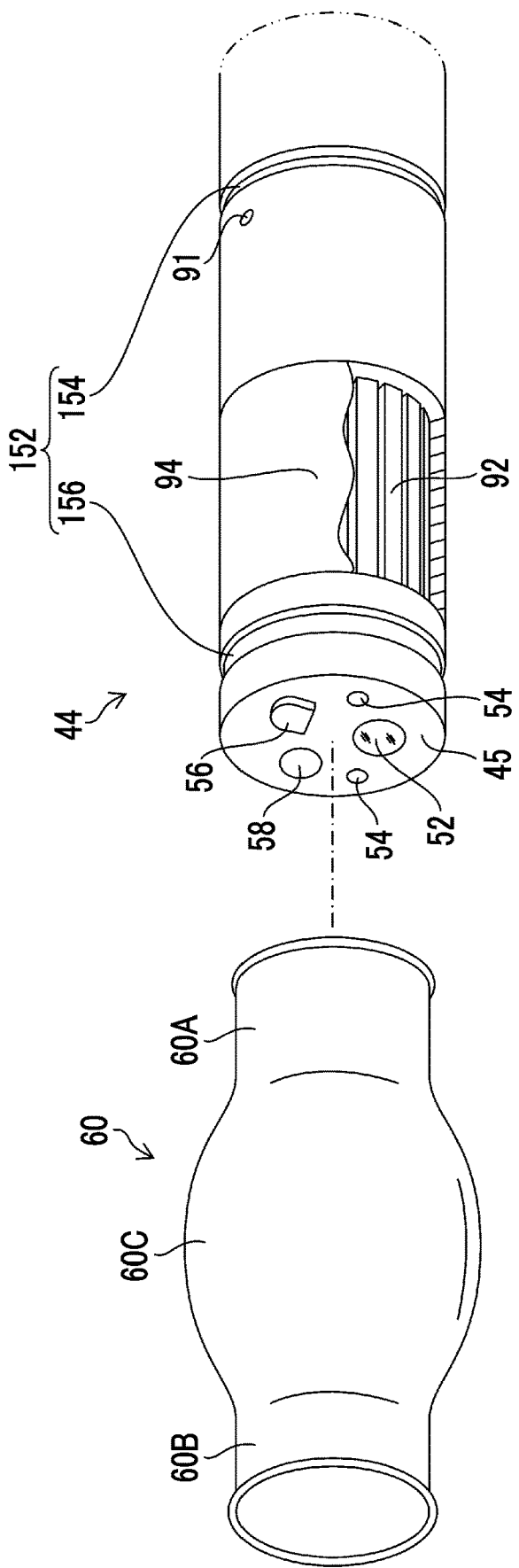
FIG. 2 is a perspective view showing a distal end portion of an insertion portion of the ultrasonic endoscope.
Figure 3:
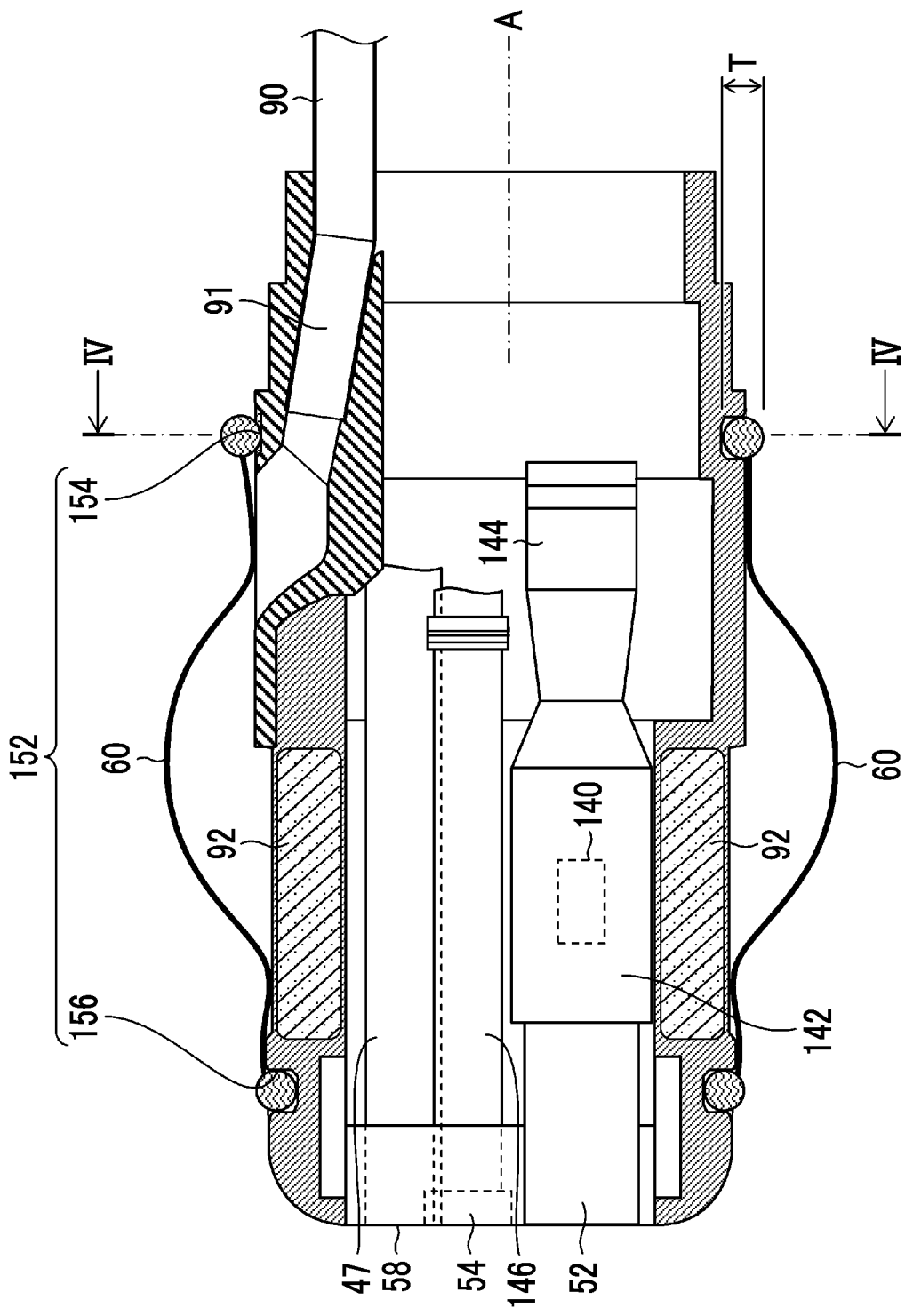
FIG. 3 is a side cross-sectional view of the distal end portion of the ultrasonic endoscope.

FIG. 1 is a system configuration view showing an example of an endoscope apparatus including the ultrasonic endoscope according to an embodiment of the present invention. FIG. 2 is a perspective view showing a distal end portion of an insertion portion of the ultrasonic endoscope. FIG. 3 is a side cross-sectional view of the distal end portion of the ultrasonic endoscope.

As shown in FIG. 1, an endoscope apparatus 1 is composed of a radial type ultrasonic endoscope 10, a balloon 60, and a balloon control device 70. The ultrasonic endoscope 10 includes an operation portion 14 and an insertion portion 12 that is connected to the operation portion 14 and that is inserted into a body. A universal cord 16 is connected to the operation portion 14. The universal cord 16 branches at an intermediate portion, and one of branches thereof is attachably and detachably connected to an ultrasonic observation device 17 that generates an ultrasonic tomographic image. An ultrasonic diagnosis image generated by the ultrasonic observation device 17 is displayed on a monitor 50. In addition, a distal end of the other of the branches of the universal cord 16 is provided with an LG connector 18. The LG connector 18 is attachably and detachably connected to a light source device 20, so that illumination light is sent to illumination windows 54 provided at the distal end of the insertion portion 12. In addition, an electric connector 24 is connected to the LG connector 18 via a cable 22, and the electric connector 24 is attachably and detachably connected to a processor 26.

On the operation portion 14, an air/water supply button 28, a suction button 30, a shutter button 32, and a function switching button 34 are arranged to be parallel, and the operation portion 14 is provided with a pair of angle knobs 36 and 36.

The insertion portion 12 is composed of a soft portion 40, a bendable portion 42, and a distal end portion 44 disposed in this order from the operation portion 14 side. The soft portion 40 is configured by covering an outer periphery of a spirally wound metal plate with a net to coat the outer periphery and has sufficient flexibility.

The bendable portion 42 is configured to be remotely curved in a case where the angle knobs 36 and 36 of the operation portion 14 are rotated. For example, regarding the bendable portion 42, a plurality of cylindrical nodal rings are rotatably connected to each other by pins, and a plurality of operation wires are inserted into the nodal rings to be guided by the pins. In addition, in a case where the operation wires are pushed or pulled, the nodal rings rotationally move, so that the bendable portion 42 is bent. It is possible to cause the distal end portion 44 to face a desired direction by bending the bendable portion 42.

As shown in FIG. 2, on an outer peripheral surface of the distal end portion 44, an ultrasonic transducer 94 including an ultrasonic wave transmission/reception surface, in which a plurality of ultrasound oscillators 92 for acquisition of an ultrasonic tomographic image are arranged to be parallel, is disposed. The ultrasonic transducer 94 emits ultrasonic waves toward an observation target site and receives an echo signal thereof. In addition, in the case of an ultrasonic tomographic examination, the balloon 60 is mounted on the outer peripheral surface of the distal end portion 44 such that the balloon 60 covers the ultrasonic transducer 94.

As shown in FIG. 2, a distal end surface 45 of the distal end portion 44, which is closer to a distal end side than the ultrasonic transducer 94, is provided with an observation window (observation system) 52, illumination windows (illumination system) 54 and 54, an air and water supply nozzle 56, and a treatment tool outlet port 58. In addition, as shown in FIG. 3, an observation optical system and an imaging element 140 such as a complementary metal oxide semiconductor (CMOS) or a charge coupled device (CCD) are disposed behind the observation window 52 via a prism (not shown), and a signal cable 144 is connected to a substrate 142 that supports the imaging element 140. The signal cable 144 is inserted into the insertion portion 12, the operation portion 14, the universal cord 16, and the like and extends up to the electric connector 24 to be connected to the processor 26. Therefore, an observed image captured via the observation window 52 is formed on a light-receiving surface of the imaging element 140 and is converted into an electric signal. The electric signal is output to the processor 26 via the signal cable 144 and is converted into video signals. Accordingly, an observation image is displayed on the monitor 50 connected to the processor 26.

As shown in FIG. 3, illumination optical systems and emission ends of light guides 146 are disposed behind the illumination windows 54. The light guides 146 are inserted into the insertion portion 12, the operation portion 14, and the universal cord 16, and incidence ends thereof are disposed in the LG connector 18. Therefore, in a case where the LG connector 18 is connected to the light source device 20, illumination light emitted from the light source device 20 is transmitted to the illumination optical systems via the light guides 146 and is emitted forward from the illumination windows 54.

The air and water supply nozzle 56 provided at the distal end portion 44 communicates with a valve (not shown) operated by means of the air/water supply button 28. The valve communicates with an air/water supply connector 48 provided at the LG connector 18. An air/water supply unit (not shown) is connected to the air/water supply connector 48 for supply of air and water. Therefore, in a case where the air/water supply button 28 is operated, air or water is jetted toward the observation window 52 from the air and water supply nozzle 56.

The treatment tool outlet port 58 provided at the distal end portion 44 communicates with a treatment tool insertion portion 46 via a treatment tool insertion channel 47. Therefore, it is possible to draw a treatment tool such as forceps out of the treatment tool outlet port 58 by inserting the treatment tool through the treatment tool insertion portion 46. In addition, the treatment tool outlet port 58 communicates with a valve (not shown) operated by means of the suction button 30, and the valve is connected to a suction connector 49 of the LG connector 18. Therefore, it is possible to suck a lesion portion or the like through the treatment tool outlet port 58 by connecting a suction unit (not shown) to the suction connector 49 and by operating the suction unit by means of the suction button 30.

An outer periphery of the distal end portion 44 of the insertion portion 12 of the ultrasonic endoscope 10 includes a balloon attachment portion 152 to which the balloon 60 is attachably and detachably attached. The balloon attachment portion 152 includes a first balloon groove 154 that is provided close to proximal ends of the ultrasound oscillators 92 and that is provided over the outer periphery of the distal end portion 44 and a second balloon groove 156 that is provided close to distal ends of the ultrasound oscillators 92 and that is provided over the outer periphery of the distal end portion 44. The balloon 60 is formed of an elastic material such as silicon rubber. The balloon 60 includes a first tubular portion 60A that is mounted on the first balloon groove 154, a second tubular portion 60B that is mounted on the second balloon groove 156, and a balloon main body 60C that is provided between the first tubular portion 60A and the second tubular portion 60B. The first tubular portion 60A and the second tubular portion 60B are formed in a substantially tubular shape narrower than the balloon main body 60C.

The insertion portion 12 is inserted into the balloon 60, and the balloon 60 is disposed on the first balloon groove 154 and on the second balloon groove 156 of the balloon attachment portion 152. The first balloon groove 154 and the second balloon groove 156 are provided in accordance with positions of end portions of the first tubular portion 60A and the second tubular portion 60B of the balloon 60 that are mounted thereon, and the end portions of the first tubular portion 60A and the second tubular portion 60B are fitted to the first balloon groove 154 and to the second balloon groove 156, respectively. Before the first tubular portion 60A and the second tubular portion 60B are mounted, inner diameters of the first tubular portion 60A and the second tubular portion 60B are smaller than an outer diameter of the insertion portion 12 of the ultrasonic endoscope 10. In a case where the balloon 60 is mounted on the insertion portion 12, an elastic force of the first tubular portion 60A and an elastic force of the second tubular portion 60B act inward in a radial direction of the insertion portion 12. That is, the first tubular portion 60A and the second tubular portion 60B that are expanded by being mounted on the insertion portion 12 contract to return to their original sizes. Because of the contractile forces of the first tubular portion 60A and the second tubular portion 60B, the balloon 60 is held at a predetermined position on the insertion portion 12.

The distal end portion 44 includes an entrance and exit way 91 of a communication path 90 that opens into an inner space of the balloon 60 attached to the balloon attachment portion 152, the entrance and exit way 91 being disposed closer to the proximal end side than the ultrasound oscillators 92 and closer to the distal end side than the first balloon groove 154. Through the communication path 90, a fluid is supplied or sucked with respect to the inner space of the balloon 60 via the entrance and exit way 91. Examples of the fluid include degassed water as an ultrasonic wave transmitting medium. Degassed water is supplied into the balloon 60 to inflate the balloon and to bring the balloon into contact with an observation target site in a body. Accordingly, air is removed from between the observation target site and the ultrasonic transducer 94, that is, from an ultrasonic wave scanning region, and thus attenuation of ultrasonic waves and of echo signals is prevented. Note that in a case where the insertion portion 12 is to be pulled out from the inside of the body of a subject, the degassed water in the balloon 60 is discharged from the communication path 90 so that the balloon 60 contracts.

The communication path 90 communicates with a balloon air supply port 38 of the operation portion 14 shown in FIG. 1. A tube 80 of FIG. 1 is connected to the balloon air supply port 38, and the balloon control device 70 is connected to the balloon air supply port 38 via the tube 80. The balloon control device 70 is a device that supplies a fluid to the balloon 60 and that sucks the fluid, and a fluid can be supplied to and sucked from the balloon 60 with the balloon control device 70 supplying or sucking the fluid. The balloon 60 inflates into a substantially spherical shape in a case where the fluid is supplied thereto, and the balloon 60 clings around an outer surface of the insertion portion 12 in a case where the fluid is sucked.

As shown in FIG. 1, the balloon control device 70 is mainly composed of a device main body 72 and a hand switch 74 for remote control. A power switch SW1, a stop switch SW2, and a pressure display unit 76 are provided on a front surface of the device main body 72. The pressure display unit 76 is a panel that displays a pressure value of the balloon 60, and in a case where an abnormality such as a rupture of the balloon occurs, an error code is displayed on the pressure display unit 76.

The tube 80 through which a fluid is supplied to and sucked from the balloon 60 is connected to the front surface of the device main body 72. A backflow prevention unit 82 for preventing backflow of a body fluid in the case of the rupture of the balloon 60 is provided at a connection portion between the tube 80 and the device main body 72. The backflow prevention unit 82 is configured by incorporating a filter for gas-liquid separation into a hollow disk-shaped case (not shown) attachably and detachably mounted on the device main body 72, and the filter prevents liquid from flowing into the device main body 72.

Meanwhile, the hand switch 74 is provided with various switches. For example, a stop switch similar to the stop switch SW2 on the device main body 72 side, an ON/OFF switch for issuing an instruction to increase and decrease the pressure of the balloon 60, a pause switch for maintaining the pressure of the balloon 60, and the like are provided. The hand switch 74 is electrically connected to the device main body 72 via a cord 84. Note that, although not shown in FIG. 1, the hand switch 74 is provided with a display unit showing the state of air supply or the state of air discharge of the balloon 60.

The balloon control device 70 supplies a fluid to the balloon 60 to inflate the balloon 60, and controls the pressure value thereof to be a constant value so as to keep the balloon 60 in an inflated state. In addition, the fluid is sucked from the balloon 60 so that the balloon 60 contracts, and the pressure value thereof is controlled to be a constant value such that the balloon 60 is kept in a contracted state.

The balloon control device 70 is connected to a balloon dedicated monitor 86, and the pressure value or the state of inflation and contraction of the balloon 60 is displayed on the balloon dedicated monitor 86 in a case where the balloon 60 is inflated and contracted. Note that the pressure value and the state of inflation and contraction of the balloon 60 may be displayed on the monitor 50 while being superimposed on an observation image of the ultrasonic endoscope 10 and displayed.

As shown in FIG. 3, regarding the communication path 90, the entrance and exit way 91 of the communication path 90 is formed to be diagonally inclined with respect to a longitudinal axis A of the insertion portion 12, and a portion of the communication path 90 that is closer to the proximal end side than the entrance and exit way 91 is formed to be parallel to the longitudinal axis of the insertion portion 12. Since the entrance and exit way 91 of the communication path 90 is formed to be diagonally inclined with respect to the longitudinal axis of the insertion portion 12, a cleaning brush inserted from a proximal end side of the communication path 90 can be inserted along the entrance and exit way 91 of the communication path 90 in a case where the communication path 90 is to be cleaned by means of the cleaning brush. Therefore, a body fluid, residue, and the like in the vicinity of the entrance and exit way 91 can be efficiently cleaned with the cleaning brush.

Figure 4:
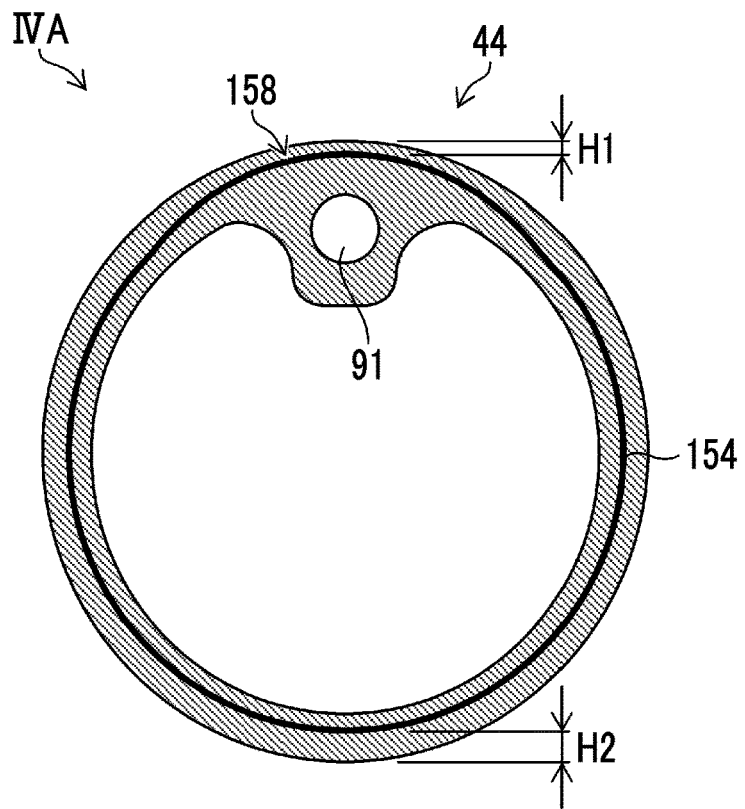
FIG. 4 is a cross-sectional view taken along line IV-IV of FIG. 3.
Figure 4:
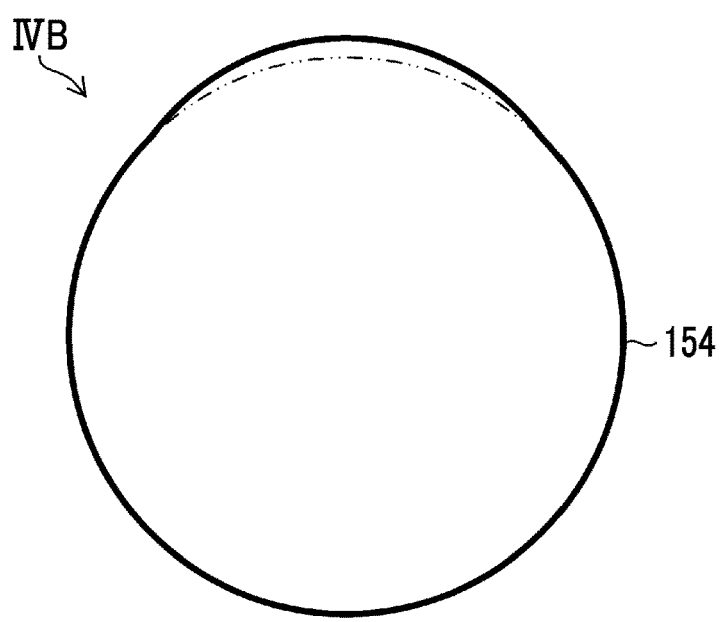

FIG. 4 shows cross-sectional views (cross-sectional view orthogonal to longitudinal axis of insertion portion 12) taken along line IV-IV (position of first balloon groove 154) of FIG. 3. In a cross section IVA, contents other than the entrance and exit way of the communication path 90 in the distal end portion 44 are not shown. In addition, a cross section IVB is a view showing only the shape of a bottom surface of the first balloon groove 154 shown in the cross section IVA. As shown in FIG. 4, the outer shape of the distal end portion 44 is a circular shape. As seen in a cross section, the shape of the bottom surface of the first balloon groove 154 is a shape obtained by swelling a portion of a circular shape formed along the outer shape of the distal end portion 44 to an outer side. Since a portion of the shape of the bottom surface of the first balloon groove 154 is swollen toward the outer side, the first balloon groove 154 includes a shallow groove portion 158, of which a groove depth is smaller than other portions, in a circumferential direction of the distal end portion 44.

Since the first balloon groove 154 includes the shallow groove portion 158, it is possible to provide a space in an internal region in the distal end portion 44 corresponding to the size of a region where the groove depth is made small. In the present embodiment, the entrance and exit way 91 of the communication path 90 is provided in an internal region of the shallow groove portion 158, and thus it is possible to form the entrance and exit way 91 of the communication path 90 to be diagonally inclined with respect to the longitudinal axis of the insertion portion 12 without changing the position of the first balloon groove 154 in a direction along the longitudinal axis and without changing the outer shape of the distal end portion 44.

Figure 5:
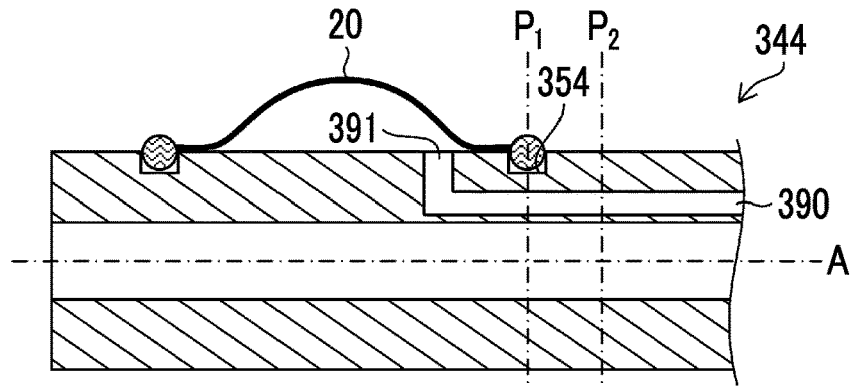
FIG. 5 is a schematic view showing comparison between a balloon attachment portion of the distal end portion of the present embodiment and balloon attachment portions of distal end portions of comparative examples.
Figure 5:
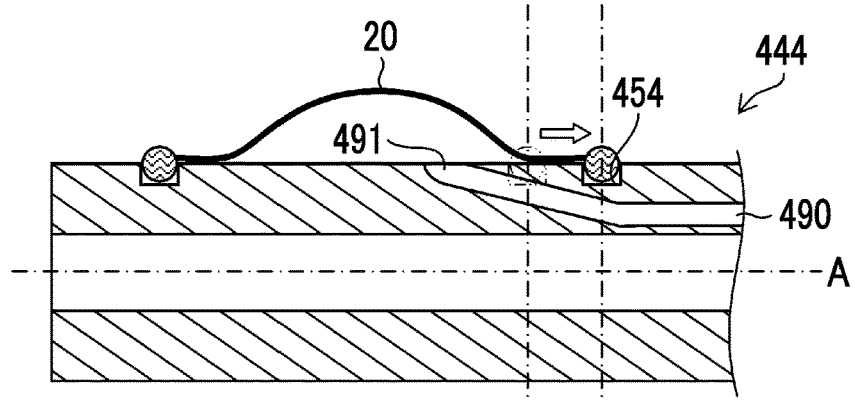
Figure 5:
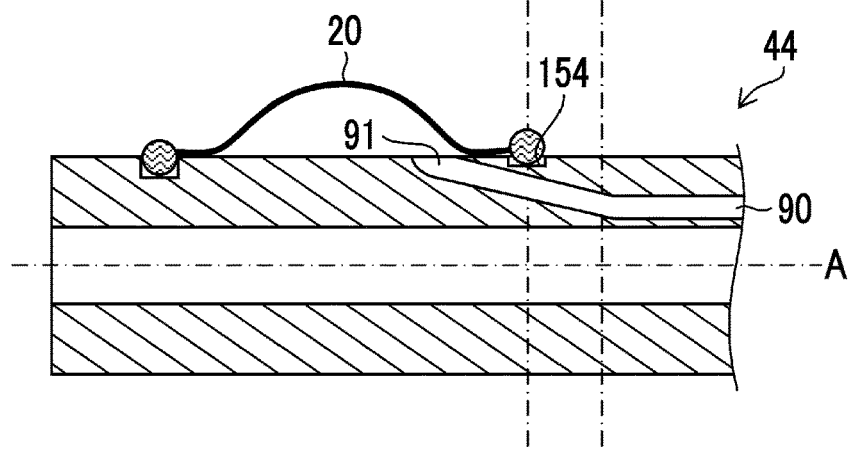

FIG. 5 is a conceptual view showing comparison between the balloon attachment portion of the distal end portion of the present embodiment and balloon attachment portions of distal end portions of comparative examples. In the case of a distal end portion 344 of Comparative Example 1, the communication path 390 is formed from a proximal end side of the distal end portion 344 to be parallel with the longitudinal axis A of the distal end portion 344, and an entrance and exit way 391 is formed to be perpendicular to the longitudinal axis A. In this case, in a case where a communication path 390 is to be cleaned by means of a cleaning brush from the proximal end side, it is difficult to insert a cleaning brush up to the entrance and exit way 391 and to clean the communication path 390.

Meanwhile, in the case of a distal end portion 444 of Comparative Example 2, an entrance and exit way 491 of a communication path 490 is formed to be diagonally inclined with respect to the longitudinal axis A. Accordingly, it is possible to insert a cleaning brush into the entrance and exit way 491 from a proximal end side of the communication path 490 and to perform cleaning. However, in this case, the entrance and exit way 490 formed diagonally interferes with a first balloon groove 454 to which a proximal end side end portion of the balloon 60 is attached, and thus it is necessary to change the position of the first balloon groove 454 to a position $P_2$ from a position $P_1$ of a first balloon groove 354 of the distal end portion 344 of Comparative Example 1. Therefore, in the case of the distal end portion 444, the position of attachment of a balloon on the proximal end side is separated from a distal end, and thus it is necessary to increase the length of the distal end portion 444. Accordingly, the radius of a trajectory drawn by the distal end portion in a case where the bendable portion 42 is bent is large.

However, in the case of the distal end portion 44 of the present embodiment, the first balloon groove 154 is provided with the shallow groove portion 158, and the entrance and exit way 91 of the communication path 90 is provided in the internal region thereof, so that interference between the entrance and exit way 91 and the first balloon groove 154 can be prevented. Therefore, the first balloon groove 154 can be provided at the same position $P_1$ as in the case of the distal end portion 344. Therefore, it is possible to prevent the length of the distal end portion 44 from becoming large even in a case where the entrance and exit way 91 is formed diagonally.

In addition, in a case where the first balloon groove 154 is provided with the shallow groove portion 158 and the entrance and exit way 91 of the communication path 90 is disposed inside the shallow groove portion 158 as in the present embodiment, it is possible to move the entrance and exit way 91 of the communication path 90 in an outward direction inside the distal end portion 44 without changing the arrangement of internal components in the distal end portion 44.

As described above, in the present embodiment, the first balloon groove 154 of the distal end portion 44 is provided with the shallow groove portion 158 so that the entrance and exit way 91 of the communication path 90 is formed to be diagonally inclined without the position of the first balloon groove 154 being moved to the proximal end side. Therefore, it is possible to achieve the configuration of the present embodiment without changing the outer shape of the distal end portion 44, and thus it is possible to achieve a configuration in which the central axis of the ultrasound oscillators 92 in a longitudinal direction and the central axis of the distal end portion 44 in a longitudinal direction coincide with each other as shown in FIG. 2. Note that the meaning of "the central axis of the ultrasound oscillators in the longitudinal direction and the central axis of the distal end portion in the longitudinal direction coincide with each other" is not limited to a state where the central axes completely coincide with each other, and variations of the central axes caused by manufacturing errors are included in the scope of the invention.

In addition, the groove depth of the second balloon groove 156 of the balloon attachment portion 152, which is provided closer to the distal end side than the ultrasound oscillators 92, is uniform in the circumferential direction of the distal end portion 44. Note that the meaning of "the depth is uniform in the circumferential direction" is not limited to a state of being completely uniform in the circumferential direction, and variations of the depth caused by manufacturing errors are included in the scope of the invention. It is possible to make a balloon attached to the distal end portion 44 less likely to fall off by making the depth of the second balloon groove 156 uniform in the circumferential direction.

The depth of the first balloon groove 154 can be, for example, as follows. Regarding the first balloon groove 154, a depth H1 of the shallow groove portion 158 can be set to be equal to or larger than 0.1 mm and equal to or smaller than 0.2 mm, and a depth H2 of a portion other than the shallow groove portion 158 can be set to be equal to or larger than 0.45 mm and equal to or smaller than 0.55 mm. In addition, a thickness T of lips of the first tubular portion 60A and the second tubular portion 60B of the balloon 60 can be set to be φ1.5 mm. The thickness T of the lips of the first tubular portion 60A and the second tubular portion 60B of the balloon 60 and the depth H2 of the first balloon groove 154 are equal to or larger than ¼ and equal to or smaller than ⅓ of the lips of the first tubular portion 60A and the second tubular portion 60B of the balloon 60 at the deepest portion of the first balloon groove 154. The depth H1 of the shallow groove portion 158 is preferably set to such a depth that the balloon is not shifted or that the balloon does not fall off, with respect to the lips of the first tubular portion 60A and the second tubular portion 60B of the balloon 60.

As described above, according to the present embodiment, it is possible to prevent the length of the distal end portion 44 from being large in the direction along the longitudinal axis, and it is possible to improve the brush cleanability of the communication path 90.

Although the ultrasonic endoscope according to the embodiment of the present invention has been described above, the present invention is not limited to the above examples, and some improvements or modifications may be made without departing from the gist of the present invention. Hereinafter, a modification example will be described.

Modification Example

Figure 6:
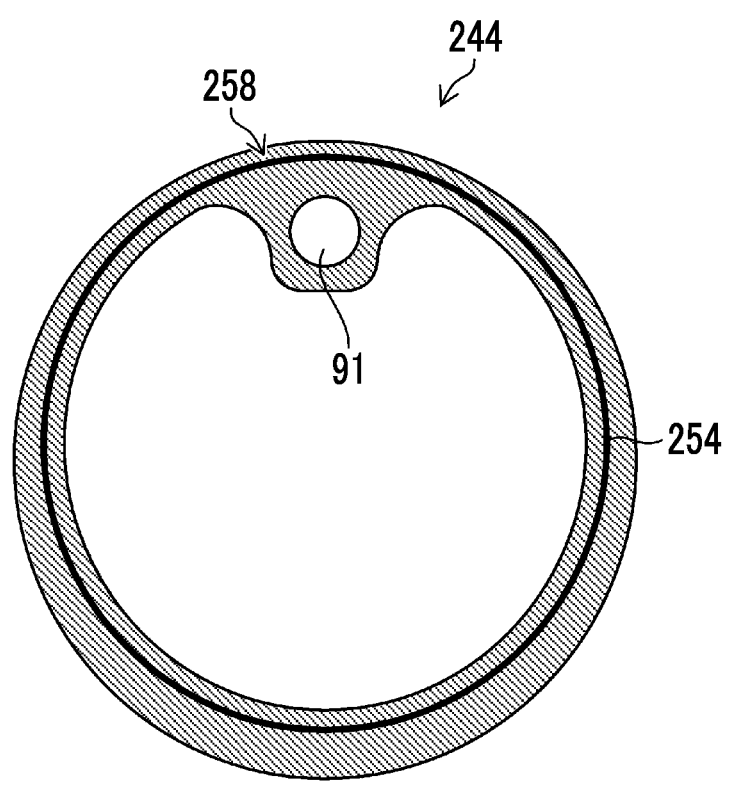
FIG. 6 is a cross-sectional view showing a modification example of a distal end portion of an ultrasonic endoscope.

FIG. 6 is a cross-sectional view showing a modification example of a distal end portion of an ultrasonic endoscope. In the case of the ultrasonic endoscope of the modification example, the internal shape of a distal end portion 244 is a circular shape as seen in the cross-sectional view and is disposed to be offset from the outer shape of the distal end portion 244. In addition, the shape of the bottom surface of a first balloon groove 254 is a circular shape and is disposed to be offset from the outer shape of the distal end portion 244.

Since an inner space and the first balloon groove 254 have the circular shapes as in the related art and are disposed to be offset from the outer shape of the distal end portion 244, a shallow groove portion 258 can be formed in the direction of offset. Since the inner space is also offset, the entrance and exit way 91 of the communication path 90 can be disposed closer to an outer side than in the related art. Accordingly, the entrance and exit way 91 of the communication path 90 can be formed to be diagonally inclined without the position of the first balloon groove 254 being moved to the proximal end side with respect to the longitudinal axis of the distal end portion 44. Therefore, it is possible to prevent the length of the distal end portion 244 from being large and to clean the communication path 90 with a cleaning brush. In addition, since there is no change in shape of the inner space of the distal end portion, it is not necessary to change the arrangement inside the ultrasonic endoscope.

EXPLANATION OF REFERENCES

1: Endoscope apparatus
10: Ultrasonic endoscope
12: Insertion portion
14: Operation portion
16: Universal cord
17: Ultrasonic observation device
18: LG connector
20: Light source device
22: Cable
24: Electric connector
26: Processor
28: Air/water supply button
30: Suction button
32: Shutter button
34: Function switching button
36: Angle knob
38: Balloon air supply port
40: Soft portion
42: Bendable portion
44, 244: Distal end portion
45: Distal end surface
46: Treatment tool insertion portion
47: Treatment tool insertion channel
48: Air/water supply connector
49: Suction connector
50: Monitor
52: Observation window
54: Illumination window
56: Air and water supply nozzle
58: Treatment tool outlet port
60: Balloon
60A: First tubular portion
60B: Second tubular portion
60C: Balloon main body
70: Balloon control device
72: Device main body
74: Hand switch
76: Pressure display unit
80: Tube
82: Backflow prevention unit
84: Cord
86: Balloon dedicated monitor
90, 390, 490: Communication path
91, 391, 491: Entrance and exit way
92: Ultrasound oscillator
94: Ultrasonic transducer
140: Imaging element
142: Substrate
144: Signal cable
146: Light guide
152: Balloon attachment portion
154, 254, 354, 454: First balloon groove
156: Second balloon groove
158, 258: Shallow groove portion

What is claimed is:
1. A radial type ultrasonic endoscope in which an ultrasound oscillator is provided at a distal end portion of an insertion portion and in which an observation system and an illumination system are disposed closer to a distal end side than the ultrasound oscillator, wherein the distal end portion includes
- a balloon attachment portion for attachably and detachably attaching a balloon to the distal end portion, the balloon attachment portion including a first balloon groove that is provided over an outer periphery of the distal end portion at least on a proximal end side of the ultrasound oscillator, and
- a communication path for supply or suction of a fluid with respect to an inner space of the balloon attached to the distal end portion, the communication path including an entrance and exit way that is open into the inner space of the balloon, the entrance and exit way of the communication path is formed to be diagonally inclined with respect to a longitudinal axis of the insertion portion, the first balloon groove includes a shallow groove portion that is formed to have a groove depth smaller than other portions in a circumferential direction of the distal end portion, and the entrance and exit way of the communication path is provided in an internal region of the distal end portion where the shallow groove portion is formed.

2. The ultrasonic endoscope according to claim 1, wherein the balloon attachment portion includes a second balloon groove that is provided over the outer periphery of the distal end portion on a distal end side of the ultrasound oscillator, and
a depth of the second balloon groove is uniform in the circumferential direction of the distal end portion.

3. The ultrasonic endoscope according to claim 1, wherein, in a cross section orthogonal to the longitudinal axis of the insertion portion, a shape of a bottom surface of the first balloon groove is a shape obtained by swelling a circle toward a position where the entrance and exit way is provided.

4. The ultrasonic endoscope according to claim 1, wherein a central axis of the ultrasound oscillator and a central axis of the distal end portion coincide with each other.

5. The ultrasonic endoscope according to claim 1, wherein a portion of the communication path that is closer to the proximal end side than the entrance and exit way is formed to be parallel with the longitudinal axis of the insertion portion.

* * * * *